US00PP34152P2

(12) United States Plant Patent
Barnes

(10) Patent No.: US PP34,152 P2
(45) Date of Patent: Apr. 19, 2022

(54) ***PETUNIA* PLANT NAMED 'WNPESVJAZ'**

(50) Latin Name: ***Petunia* X *hybrida***
Varietal Denomination: WNPESVJAZ

(71) Applicant: Brent D. Barnes, Riverside, CA (US)

(72) Inventor: Brent D. Barnes, Riverside, CA (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 17/371,504

(22) Filed: Jul. 9, 2021

(51) Int. Cl.
*A01H 6/82* (2018.01)
*A01H 5/02* (2018.01)

(52) U.S. Cl.
USPC ..... Plt./356.22

(58) Field of Classification Search
USPC ..... Plt./356.22
See application file for complete search history.

*Primary Examiner* — Annette H Para
(74) *Attorney, Agent, or Firm* — C. Anne Whealy

(57) ABSTRACT

A new and distinct *Petunia* plant named 'WNPESVJAZ', characterized by its upright to outwardly spreading and mounding to eventually trailing plant habit; vigorous growth habit and rapid growth rate; freely branching habit; dense and bushy plant form; early and freely flowering habit; single-type flowers that are vivid reddish purple in color; and excellent garden performance.

2 Drawing Sheets

Figure 1:
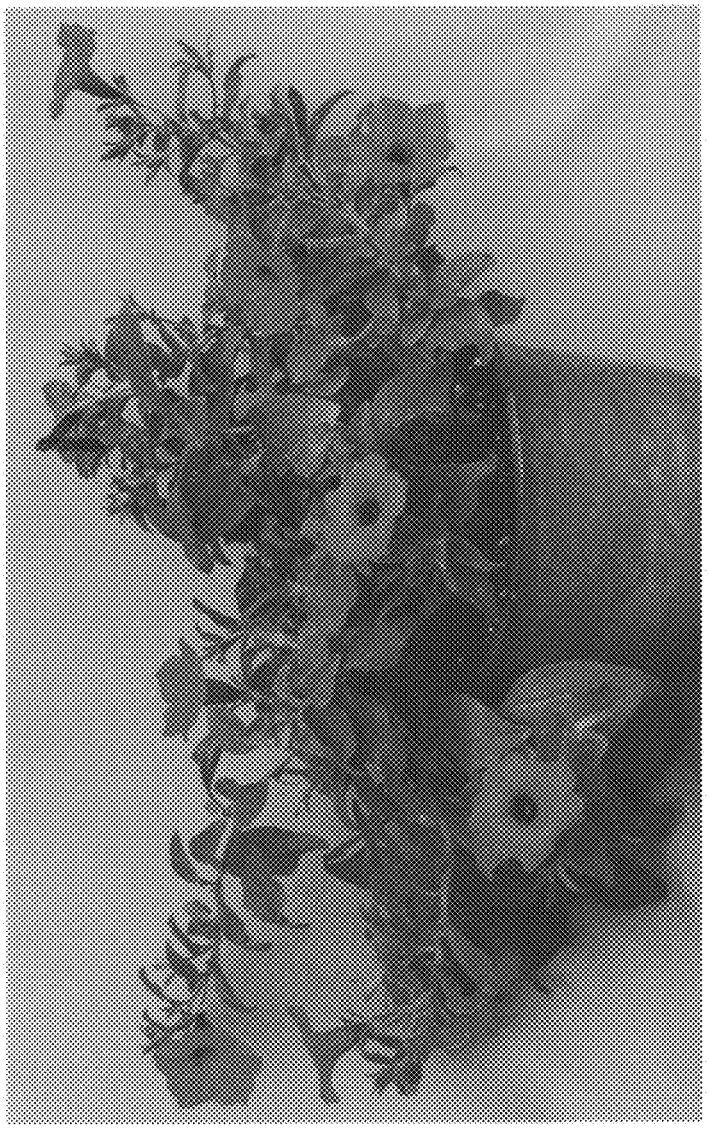

Botanical designation: *Petunia* X *hybrida.*
Cultivar Denomination: 'WNPESVJAZ'.

BACKGROUND OF THE INVENTION

The present invention relates to a new and distinct cultivar of *Petunia* plant, botanically known as *Petunia* X *hybrida* and hereinafter referred to by the name 'WNPESVJAZ'.

The new *Petunia* plant is a product of a planned breeding program conducted by the Inventor in Bonsall, Calif. The objective of the breeding program is to create new vigorous, freely-branching and uniformly mounding *Petunia* plants with early and freely flowering habit, attractive flowers and good garden performance.

The new *Petunia* plant originated from a cross-pollination made by the Inventor on Feb. 12, 2018 in Bonsall, Calif. of a proprietary selection of *Petunia* X *hybrida* identified as code number 15PB559-04, not patented, as the female, or seed, parent with a proprietary selection of *Petunia* X *hybrida* identified as code number 15PB626-01, not patented, as the male, or pollen, parent. The new *Petunia* plant was discovered and selected by the Inventor as a single flowering plant within the progeny of the stated cross-pollination in a controlled greenhouse environment in Bonsall, Calif. on Aug. 2, 2018.

Asexual reproduction of the new *Petunia* plant by vegetative terminal cuttings in a controlled greenhouse environment in Bonsall, Calif. since Aug. 6, 2018 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNPESVJAZ'. These characteristics in combination distinguish 'WNPESVJAZ' as a new and distinct *Petunia* plant:

1. Upright to outwardly spreading and mounding to eventually trailing plant habit.
2. Vigorous growth habit and rapid growth rate.
3. Freely branching habit; dense and bushy plant form.
4. Early and freely flowering habit.
5. Single-type flowers that are vivid reddish purple in color.
6. Excellent garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are more mounding than and not as spreading as plants of the female parent selection.
2. Leaves of plants of the new *Petunia* are narrower and darker green in color than leaves of plants of the female parent selection.
3. Plants of the new *Petunia* have smaller flowers than plants of the female parent selection.
4. Flowers of plants of the new *Petunia* are darker reddish purple in color than flowers of plants of the female parent selection.

Plants of the new *Petunia* can be compared to plants of the male parent selection. In side-by-side comparisons, plants of the new *Petunia* differ primarily from plants of the male parent selection in the following characteristics:

1. Plants of the new *Petunia* are more outwardly spreading than and not as upright as plants of the male parent selection.

2. Leaves of plants of the new *Petunia* are broader and darker green in color than leaves of plants of the male parent selection.
3. Plants of the new *Petunia* have larger flowers than plants of the male parent selection.
4. Flowers of plants of the new *Petunia* are darker reddish purple in color than flowers of plants of the male parent selection.

Plants of the new *Petunia* can be compared to plants of *Petunia* X *hybrida* 'USTUNI6001', disclosed in U.S. Plant Pat. No. 17,730. In side-by-side comparisons, plants of the new *Petunia* differ primarily from plants of 'USTUNI6001' in the following characteristics:

1. Plants of the new *Petunia* are more outwardly spreading than and not as upright as plants of 'USTUNI6001'.
2. Plants of the new *Petunia* have slightly smaller flowers than plants of 'USTUNI6001'.
3. Plants of the new *Petunia* have vivid reddish purple-colored flowers whereas plants of 'USTUNI6001' have bright pink-colored flowers.

Plants of the new *Petunia* can also be compared to plants of *Petunia* X *hybrida* 'USTUN2401M', disclosed in U.S. Plant Pat. No. 29,664. In side-by-side comparisons, plants of the new *Petunia* differ primarily from plants of 'USTUN2401M' in the following characteristics:

1. Plants of the new *Petunia* are larger than and not as compact as plants of 'USTUN2401M'.
2. Plants of the new *Petunia* have slightly larger flowers than plants of 'USTUN2401M'.
3. Plants of the new *Petunia* have vivid reddish purple-colored flowers whereas plants of 'USTUN2401M' have hot pink-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'WNPESVJAZ' grown in a container.

Figure 2:
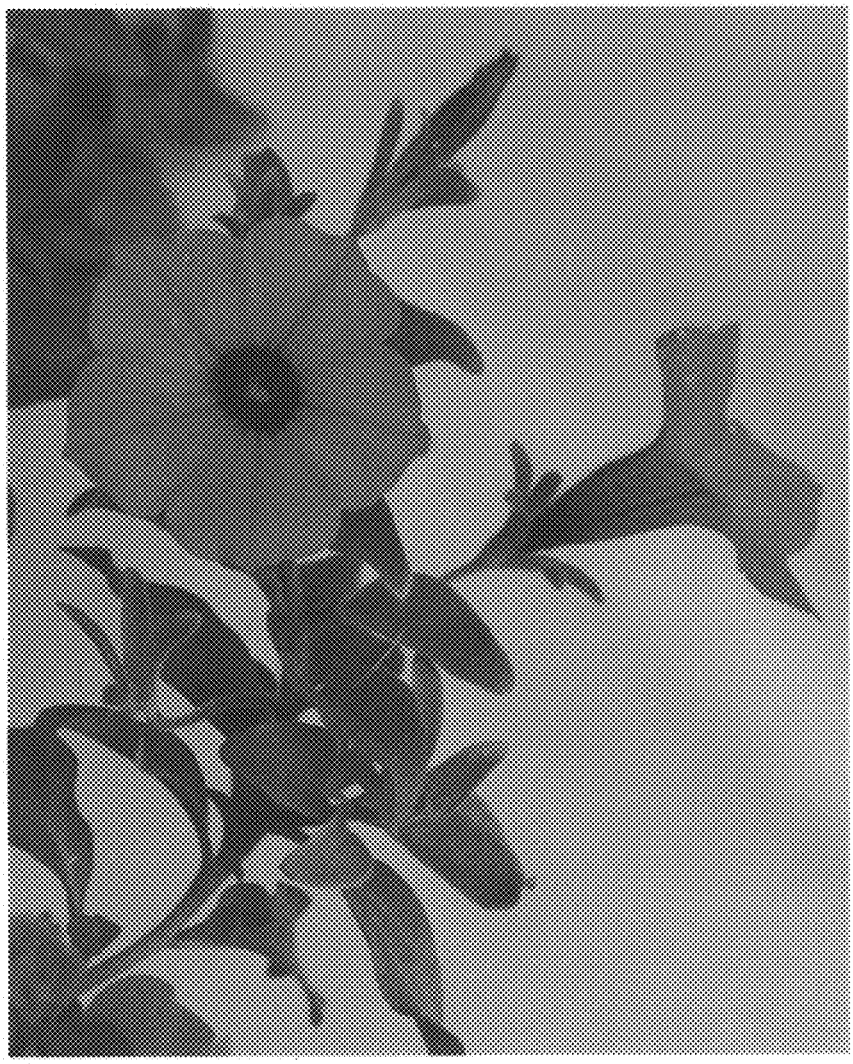

The photograph on the second sheet (FIG. 2) is a close-up view of a typical flowering plant of 'WNPESVJAZ'.

DETAILED BOTANICAL DESCRIPTION

The aforementioned photographs and following observations and measurements describe plants grown during the late summer and early autumn in 10.8-cm containers in a corrugated polycarbonate-covered greenhouse in Carlton, Mich. and under cultural practices typical of commercial *Petunia* production. During the production of the plants, day temperatures averaged 26° C., night temperatures averaged 20° C. and light levels averaged 9,290 footcandles. Plants were pinched three weeks after planting and were ten weeks from planting rooted cuttings when the photographs and description were taken. In the following description, color references are made to The Royal Horticultural Society Colour Chart, 2015 Edition, except where general terms of ordinary dictionary significance are used.

Botanical classification: *Petunia* X *hybrida* 'WNPESVJAZ'.

Parentage:

*Female, or seed, parent*.—Proprietary selection of *Petunia* X *hybrida* identified as code number 15PB559-04, not patented.

*Male, or pollen, parent*.—Proprietary selection of *Petunia* X *hybrida* identified as code number 15PB626-01, not patented.

Propagation:

*Type*.—Terminal vegetative cuttings.

*Time to initiate roots, summer*.—About three to four days at ambient temperatures ranging from 17° C. to 29° C.

*Time to initiate roots, winter*.—About five to seven days at ambient temperatures ranging from 17° C. to 21° C.

*Time to produce a rooted plant, summer*.—About three weeks at ambient temperatures ranging from 17° C. to 29° C.

*Time to produce a rooted plant, winter*.—About four weeks at ambient temperatures ranging from 17° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to outwardly spreading and mounding to eventually trailing plant habit; freely branching habit with lateral branches potentially developing at every node, dense and bushy plant form; pinching enhances development of lateral branches; vigorous growth habit and rapid growth rate.

*Plant height*.—About 12.5 cm.

*Plant diameter* (*area of spread*).—About 36 cm by 40 cm.

*Lateral branches*.—Length: About 19 cm. Diameter: About 3 mm. Internode length: About 1.5 cm to 2 cm. Strength: Moderately strong; flexible, not brittle. Aspect: Initially upright then outwardly spreading to trailing. Texture and luster: Densely pubescent; slightly glossy. Color, developing and developed: Close to 144A.

Leaf description:

*Arrangement*.—Alternate before flowering; opposite after flowers develop; leaves simple.

*Length*.—About 4.8 cm to 5.3 cm.

*Width*.—About 2.5 cm to 2.7 cm.

*Shape*.—Narrowly ovate.

*Apex*.—Acute.

*Base*.—Cuneate with obtuse tendencies.

*Margin*.—Entire, slightly undulate.

*Texture and luster, upper surface*.—Moderately pubescent, pubescence, minute; slightly glossy.

*Texture and luster, lower surface*.—Mostly glabrous with minute pubescence along veins and margins; slightly glossy.

*Venation pattern*.—Pinnate, arcuate.

*Color*.—Developing leaves, upper surface: Close to 146A. Developing leaves, lower surface: Close to 146B. Fully developed leaves, upper surface: Close to 146A; venation, close to 144A. Fully developed leaves, lower surface: Close to 146B; venation, close to 146C.

*Petioles*.—Length: About 1.25 cm to 1.5 cm. Diameter: About 2 mm to 2.5 mm. Strength: Strong, flexible. Texture and luster, upper and lower surfaces: Densely pubescent; slightly glossy. Color, upper surface: Close to 146A. Color, lower surface: Close to 146B.

Flower description:

*Flower type and flowering habit*.—Single terminal and axillary salverform flowers; flowers face mostly upward to outwardly; freely flowering habit with flowers potentially forming at every node.

*Natural flowering season*.—Long day responsive; long flowering period, plants flower from early spring until frost in the autumn, flowering continuous during this period; early flowering habit, plants begin flowering about 40 days after planting.

*Flower longevity on the plant*.—About five to seven days; petals not persistent and sepals, persistent.

*Fragrance*.—None detected.

*Flower buds*.—Length: About 1.8 cm. Diameter: About 5 mm. Shape: Oblong, elongate. Texture and luster: Pubescent; slightly glossy. Color: Sepals, close to 146A; petals, close to 83A.

*Flower diameter*.—About 3.8 cm to 4 cm.

*Flower depth* (*height*).—About 2.5 cm to 2.7 cm.

*Throat diameter*.—About 1 cm.

*Tube length*.—About 1.6 cm.

*Tube diameter, distally*.—About 1 cm.

*Tube diameter, proximally*.—About 2 mm.

*Petals*.—Quantity and arrangement: Five petals fused in a single salverform whorl. Petal lobe length (from throat): About 1.5 cm to 1.75 cm. Petal lobe width: About 1.75 cm. Petal lobe shape: Spatulate. Petal lobe apex: Broadly cuspidate. Petal lobe margin: Entire; slightly undulate. Petal lobe texture and luster, upper surface: Smooth, glabrous; velvety; matte. Petal lobe texture and luster, lower surface: Smooth, glabrous; matte. Throat texture and luster: Smooth, glabrous; slightly glossy. Tube texture and luster: Moderately pubescent; matte. Color: When opening, upper surface: Iridescent, close to 71A; midvein, close to N79A. When opening, lower surface: Close to N74C to N74D; venation, close to N79A. Fully opened, upper surface: Iridescent, close to N74A; venation, close to N74A; color does not change with subsequent development. Fully opened, lower surface: Close to N74C to N74D; venation, close to N79A; color does not change with subsequent development. Flower throat (inside): Close to N79A; venation, close to N79A. Flower tube (outside): Close to N74A to N74B; venation, close to N79A.

*Sepals*.—Quantity and arrangement: Five sepals fused in a single star-shaped whorl. Length: About 1.4 cm to 1.7 cm. Width: About 3 mm to 4 mm. Shape: Narrowly oblong. Apex: Acute to obtuse. Margin: Entire. Texture and luster, upper and lower surfaces: Moderately pubescent; slightly glossy. Color: When opening and fully developed, upper surface: Close to 146B. When opening and fully developed, lower surface: Close to 146A.

*Peduncles*.—Length: About 1.5 cm. Width: About 1 mm. Strength: Moderately strong to strong; wiry and flexible, not brittle. Angle: About 45° from stein axis. Texture and luster: Densely pubescent; slightly glossy. Color: Close to 144A; distally, slightly tinged with close to N79A.

*Reproductive organs*.—Stamens: Quantity per flower: About five. Filament length: About 1.5 cm to 1.75 cm. Filament color: Close to N79A. Anther length: About 2 mm. Anther shape: Bi-lobed. Anther color: Close to 97A. Pollen amount: Moderate. Pollen color: Close to 92A. Pistils: Quantity per flower: One. Pistil length: About 1.6 cm. Style length: About 1.5 cm. Style color: Close to 145C; distally, close to 79A. Stigma diameter: About 2 mm. Stigma shape: Round. Stigma color: Close to 200A. Ovary color: Close to 144A.

*Seeds and fruits*.—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have excellent garden performance and have been observed to tolerate rain, wind and temperatures ranging from about 1° C. to about 35° C.

It is claimed:

1. A new and distinct *Petunia* plant named 'WNPESVJAZ' as illustrated and described.

* * * * *